(12) United States Patent
Chanduszko

(10) Patent No.: US 12,318,112 B2
(45) Date of Patent: Jun. 3, 2025

(54) ENDOVASCULAR CUTTING APPARATUS

(71) Applicant: C.R. BARD, INC., Tempe, AZ (US)

(72) Inventor: Andrzej J. Chanduszko, Chandler, AZ (US)

(73) Assignee: C.R. Bard, Inc., Franklin Lakes, NJ (US)

( * ) Notice: Subject to any disclaimer, the term of this patent is extended or adjusted under 35 U.S.C. 154(b) by 765 days.

(21) Appl. No.: 17/433,676

(22) PCT Filed: Feb. 28, 2019

(86) PCT No.: PCT/US2019/019937
§ 371 (c)(1),
(2) Date: Aug. 25, 2021

(87) PCT Pub. No.: WO2020/176090
PCT Pub. Date: Sep. 3, 2020

(65) Prior Publication Data
US 2022/0039827 A1  Feb. 10, 2022

(51) Int. Cl.
*A61B 17/3207* (2006.01)
*A61B 17/22* (2006.01)

(52) U.S. Cl.
CPC ............. *A61B 17/320725* (2013.01); *A61B 2017/22051* (2013.01); *A61B 2017/320733* (2013.01)

(58) Field of Classification Search
CPC ...... A61B 17/32037; A61B 17/320725; A61B 17/320758
See application file for complete search history.

(56) References Cited

U.S. PATENT DOCUMENTS

| | | | |
|---|---|---|---|
| 5,234,450 A * | 8/1993 | Segalowitz | A61B 17/3207 606/159 |
| 2004/0193196 A1 | 9/2004 | Appling et al. | |
| 2005/0192606 A1 | 9/2005 | Paul | |
| 2006/0116701 A1 | 6/2006 | Crow | |
| 2009/0099581 A1 | 4/2009 | Kim et al. | |
| 2013/0116715 A1 | 5/2013 | Weber | |
| 2015/0272612 A1 | 10/2015 | Avneri et al. | |

* cited by examiner

*Primary Examiner* — Ashley L Fishback
(74) *Attorney, Agent, or Firm* — Dickinson Wright PLLC; Andrew D. Dorisio

(57) ABSTRACT

An apparatus for cutting a wall of a vessel (V), such as scoring or slicing a lesion (L) associated therewith. The device includes a cutter (10) with a single shaft (12) having a branched portion including at least two radially expandable arms. A first (16) of the expandable arms includes at least one blade (20) for slicing or scoring the lesion (L) when expanded. A second (18) of the expandable arms may also include a blade (20), or may have no blade. A sheath (S) may also be provided. The arm or arms with blades may also include a limiter (22) for limiting the cutting depth of the blade (20). An anchor may also be provided for anchoring the cutter (10) in the vessel (V).

18 Claims, 7 Drawing Sheets

ENDOVASCULAR CUTTING APPARATUS

INCORPORATION BY REFERENCE

All publications and patent applications mentioned in this specification are herein incorporated by reference to the same extent as if each individual publication or patent application was specifically and individually indicated to be incorporated by reference.

TECHNICAL FIELD

This disclosure pertains to devices for providing endovascular treatment and, in particular, an apparatus for cutting a vessel wall in a controlled manner, such as for slicing or scoring a lesion associated therewith.

BACKGROUND

Balloon dilatation catheters are used to treat lesions in vessels, such as by way of angioplasty. While successful for use in a variety of applications or locations in the vasculature, some situations call for a different approach in view of the possibility of "elastic recoil," which refers to the inherent resistance of a tissue to changes in shape, and the tendency of the tissue to revert to its original shape once deformed. Furthermore, some applications, and particularly those "below the knee" (BTK) involve hard calcifications, for which balloon angioplasty alone may be contraindicated. Moreover, the use of pharmacological agents to lesions for enhanced treatment may be desirable in some instances, and efficacy may be increased by actively cutting prior to application.

Accordingly, it would be desirable to provide a simple, yet effective apparatus for cutting a vessel wall and, in particular, for slicing or scoring a lesion associated therewith. Such a device would be readily useful in a variety of locations in the vasculature, including where particularly hard calcifications might be present, and conditions dictate a more reliable and effective approach than known proposals.

SUMMARY

An object of the invention is to provide an apparatus for endovascular cutting and, in particular, a cutter for cutting a vessel wall, (and more specifically, a plaque, lesion, or other obstruction) that addresses and overcomes the foregoing limitations, and possibly others that have yet to be discovered.

According to one aspect of the disclosure, an apparatus for slicing or scoring a lesion in a vessel, comprising a sheath and a cutter for projecting from the sheath in a deployed position for slicing or scoring the lesion. The cutter includes a single shaft connected to a plurality of expandable arms, including a first expandable arm having at least one blade for scoring or slicing the lesion when the cutter is in the deployed position.

In some embodiments, the plurality of expandable arms comprise at least two expandable arms forming a Y-shape at a distal end of the single shaft. The first expandable arm may include a pair of blades. A second expandable arm may include at least one blade, or may include no blade. Any of the expandable arms may include a limiter for limiting a cutting depth of the cutter in the deployed position.

The plurality of expandable arms comprise at least two expandable arms connected to the single shaft at a common bifurcation point. The cutter may comprise three, four, five, or more expandable arms connected to the single shaft.

An anchor may be provided for anchoring the cutter in the vessel. In some embodiments, the anchor comprises an expandable element. The expandable element may comprise an inflatable balloon or an expandable cage. The anchor may be attached to the cutter or the sheath.

According to a further aspect of the disclosure, an apparatus for slicing or scoring a lesion in a vessel is provided. The apparatus comprises a cutter including a single shaft having a branched portion including at least two expandable arms, a first of the expandable arms including at least one blade for slicing or scoring the lesion when expanded.

In some embodiments, the apparatus further includes a sheath for receiving the cutter. The at least two expandable arms may form a Y-shape at a distal end of the single shaft. The first expandable arm includes a pair of blades and may include at least one blade or no blades. The first expandable arm may include a limiter for limiting a cutting depth of the cutter.

The at least two expandable arms may connect to the single shaft at a common bifurcation point. The cutter may further comprise three, four, five or more expandable arms.

An anchor may be provided for anchoring the cutter in the vessel. The anchor may comprise an expandable element. The expandable element may comprise an inflatable balloon or an expandable cage. The anchor may be connected to a cutter, or an associated sheath.

In any embodiment, the cutter may comprise a shape memory material.

BRIEF DESCRIPTION OF THE DRAWING FIGURES

The above and further advantages of the invention according to the disclosure may be better understood by referring to the following description in conjunction with the accompanying drawings in which.

Figure 1:
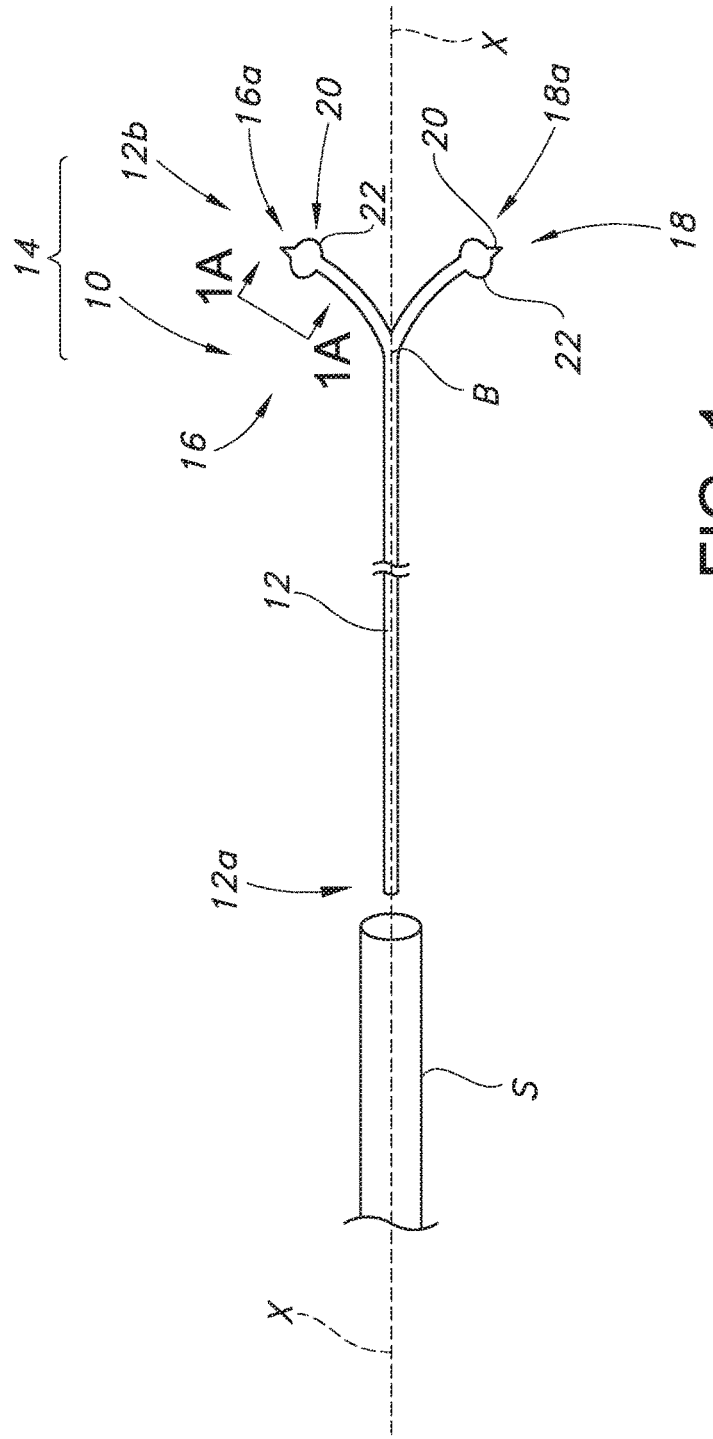
FIG. 1 illustrates one embodiment of a cutter according to the disclosure.

FIGS. 4, 5, 6, and 7 illustrate various alternative embodiments of cutters according to the disclosure;

FIGS. 8, 9, 10, and 11 illustrate various embodiments of anchors for use in connection with any or all of the disclosed cutters; and FIGS. 12-15 illustrate alternate embodiments.

The drawings are not necessarily drawn proportionally or to scale. For example, the dimensions of some of the elements may be exaggerated relative to other elements for clarity or several physical components may be included in one functional block or element. Further, sometimes reference numerals may be repeated among the drawings to indicate corresponding or analogous elements.

DETAILED DESCRIPTION

In the following detailed description, numerous specific details are set forth to provide a thorough understanding of the disclosed concepts. Those of ordinary skill in the art will know that the disclosed inventions may be practiced without these specific details. In other instances, well-known methods, procedures, components, or structures may not have been described in detail so as not to obscure the disclosed inventions.

The description provided below and in regard to the figures applies to all embodiments unless noted otherwise, and features common to each embodiment are similarly shown and numbered.

Referring first to FIG. 1, a cutter 10 according to the disclosure is illustrated. The cutter 10 includes an elongated body or shaft 12 having a proximal end 12a and a distal end 12b, which may include a tip portion 14 adapted for cutting a vessel wall. While elongated along a longitudinal axis X and in a corresponding longitudinal direction, the shaft 12 is illustrated in a compact form simply for ease of illustration, and would normally have a considerable length (e.g., 50-150 centimeters, or otherwise suitable to allow the distal end 12b to reach a treatment area of interest in the vasculature while the proximal end 12a remains accessible external to the vasculature).

Figure 1A:
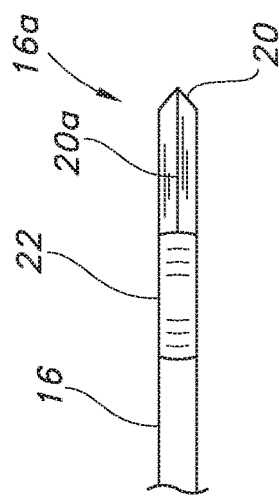
FIG. 1A illustrates a view taken from line 1A-1A of FIG. 1.

With continued reference to FIG. 1, and also FIG. 1A, it can be appreciated that the distal end 12b of the singular shaft 12 includes at least two radially extendable arms 16, 18 emanating from a common point of bifurcation B (but there could also be a single arm, as noted below). The arms 16, 18 are illustrated in a deployed position for cutting, and thus provide the cutter 10 with a Y-shaped configuration at the tip portion 14. However, the arms 16, 18 would normally be substantially aligned with the longitudinal axis X in a relaxed or non-deployed position, in which radial expansion has not occurred.

At least one of the arms, such as a first or upper arm 16 in FIG. 1, includes a distal or head 16a having a blade 20, which includes a thin, blade edge 20a of various shapes (flat, convex, chiseled, single bevel, double bevel, etc.) to provide a precision cut. The blade edge 20a may also be serrated (single or double), scalloped, chamfered, wavy, or take other shapes or forms, depending on the particular use, and more than one blade edge may be provided (such as on both a distal and a proximal side of the head 16a, or also on lateral sides thereof).

Figure 2:
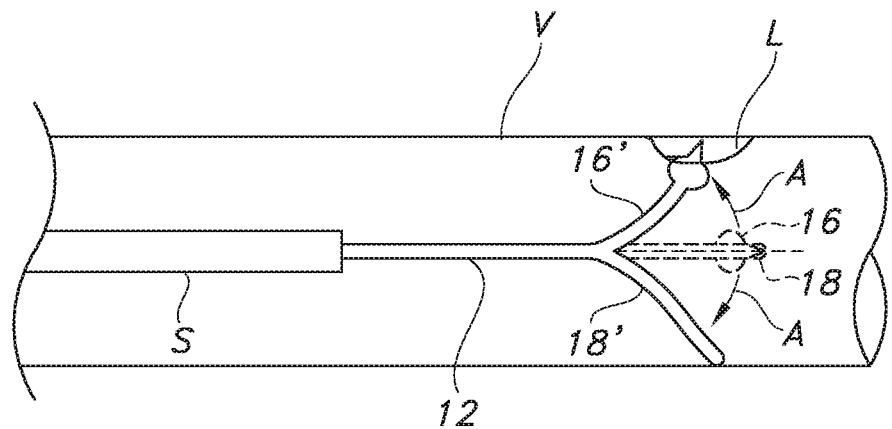
FIG. 2 is another embodiment of a cutter according to the disclosure.

In use, and with further reference to FIG. 2, the cutter 10 while protected during delivery by a covering, such as a catheter or sheath S, may be advanced into a vessel V to a treatment location, which may include a lesion L in need of scoring or slicing. At this location, the cutter 10 may be advanced from the distal end of the sheath S along axis X, and the arms 16, 18 radially expanded from a retracted condition (shown in phantom) to the deployed conditions 16', 18' farther away from axis in a radial direction for providing a slicing or scoring function. The cutter 10 may be moved about within the vessel V in order to perform the slicing or scoring function as necessary or desired, such as by manual manipulation from a point external to the associated body.

As can be appreciated, the second arm 18 in the FIG. 1 embodiment also includes a head 18a having a blade 20, which may be used for scoring or slicing within the vessel in opposition to the blade 20 associated with head 16a. However, the second arm 18 in the illustrated embodiment of FIG. 2 does not include a cutter and when expanded and thus may contact another portion of an interior wall of the vessel V to provide a counteracting or counterbalancing force for achieving the scoring or slicing operation. As can be appreciated, the cutter 10 may also be rotated about the vessel V as necessary or desired to score or slice other lesions or the like within the vessel, and may be extended or retracted as necessary (and as can be appreciated, would normally be formed of a radiopaque material or have radiopaque markers to achieved enhanced locatability under fluoroscopy or other in vivo visualization technologies).

The radial expansion of the distal portion or tip 14 may be achieved by forming at least the arms 16, 18 from a material that changes shape based on a change in ambient conditions, such as a shape memory material (e.g. Nitinol) that assumes a particular configuration based on a change in temperature (which may be achieved by supplying fluid via sheath S or based on body temperature). In particular, the use of superelastic Nitinol is possible, which would not require injection of fluid. As can be appreciated, the degree of expansion may thus be precisely controlled to ensure that the cutter 10 and, in particular, the blade edge 20a may function to slice or score a lesion in a vessel having a typical diameter, and without expanding the vessel to avoid elastic recoil. When retraction is desired, the cutter 10 may simply be withdrawn into the sheath S and the arms 16, 18 collapsed as a result. The sheath S may then be withdrawn or repositioned, as desired.

Figure 3:
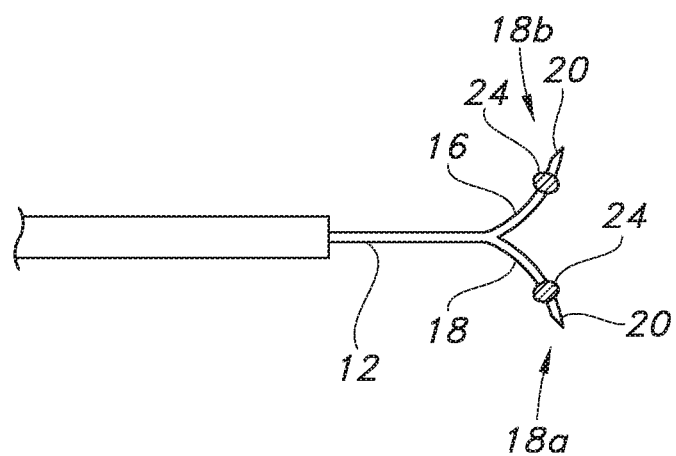
FIG. 3 is yet another embodiment of a cutter according to the disclosure.

As can be appreciated, the diameter of a vessel may be variable to a certain degree. To ensure that a proper cutting depth is achieved and, in particular, without expanding the vessel to cause elastic recoil, the cutter 10 and, specifically the arm 16 including the blade edge 20a, may optionally be provided with a limiter 22. In the examples shown in FIGS. 1 and 2, the limiter 22 comprises an oversized portion just proximal of the head 16a of the corresponding arm 16, and may be smooth or rounded so as to not provide a cutting function when contacted with material in the vessel, such as a lesion, calcification, or the like. The location of the limiter 22 may be selected to achieve a desired cutting depth, depending on the particular application. Also, the limiter 22 may take other forms, such as a generally spherical bead 24 as shown in FIG. 3, which also shows that the second arm 18 includes a blade 20 at a head end thereof.

Figure 4:
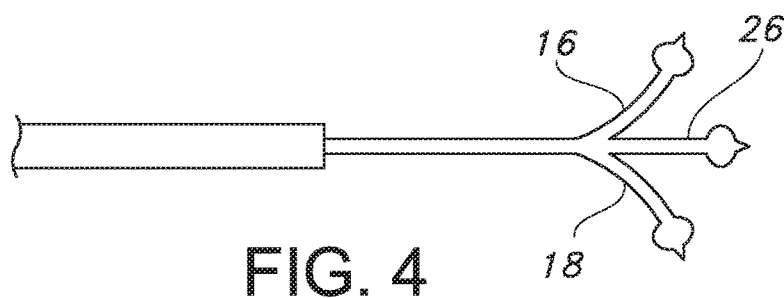
Figure 5:
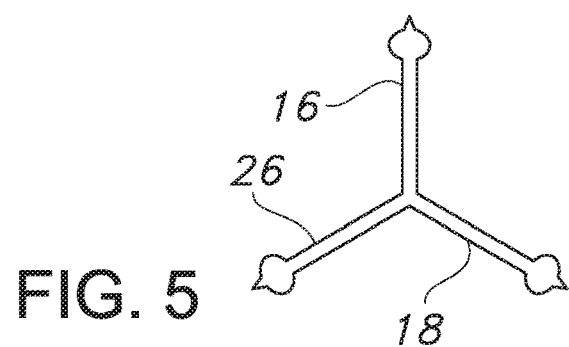
Figure 6:
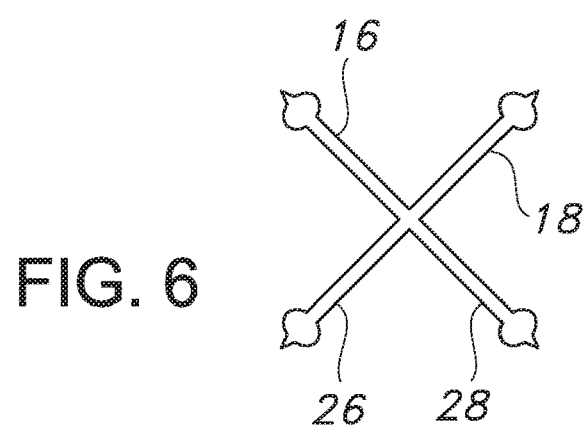
Figure 7:
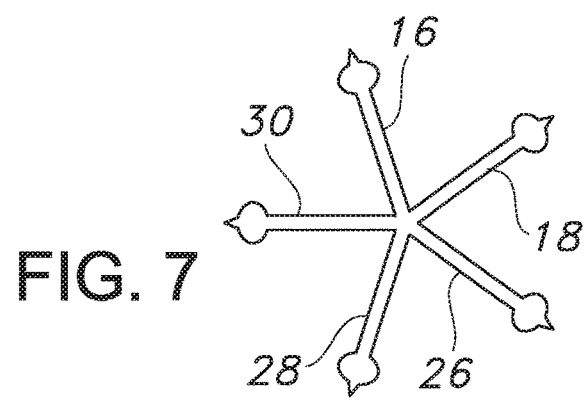

In view of the above branched (bifurcated) arrangement of arms 16, 18 when plural blades 20 are included, cutting or scoring of a lesion may occur on multiple sides of the vessel at once using the cutter 10. However, as can be appreciated, additional cutting capacity may be achieved by providing additional arms emanating from the single shaft 12. Thus, as indicated in FIGS. 4 and 5, a third arm 26 may be provided to create a trifurcated cutter 10. FIG. 6 indicates that a fourth arm 28 may be provided, and FIG. 7 indicates that a fifth arm 30 may be provided. Of course, it is possible to provide any number of arms that space will permit, and as noted, all, some, or only one of the arms provided may be adapted for slicing or scoring a lesion.

Figure 8:
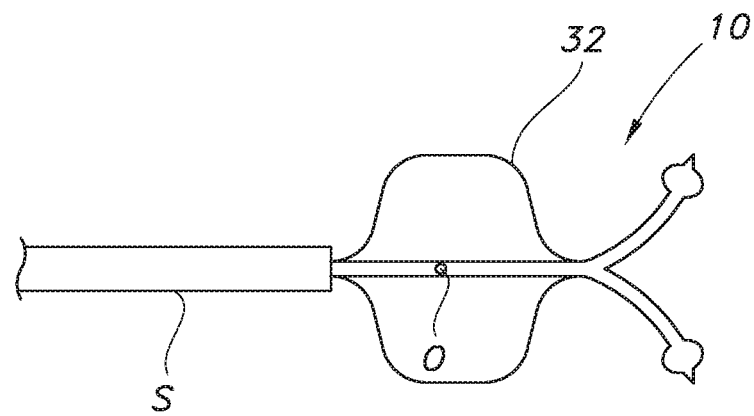

To facilitate the operation and ensure proper positioning within the vessel in a reliable manner, the cutter 10 may include an anchor. In one embodiment, as shown in FIG. 8, the anchor comprises an expandable (inflatable) balloon 32, which may be attached to the shaft 12 proximally of the point of diversion to form the arms 16, 18 (or more if present). Inflation fluid for the balloon 32 may be provided via a lumen in the shaft 12 to an outlet O within the interior compartment of the balloon 32. The balloon 32 may thus be moved through the sheath S in a collapsed or folded configuration, and then expanded within the vessel to provide a positioning function for the associated cutter 10 once expanded. The balloon 32 may be compliant, non-compliant, or semi-compliant.

Figure 9:
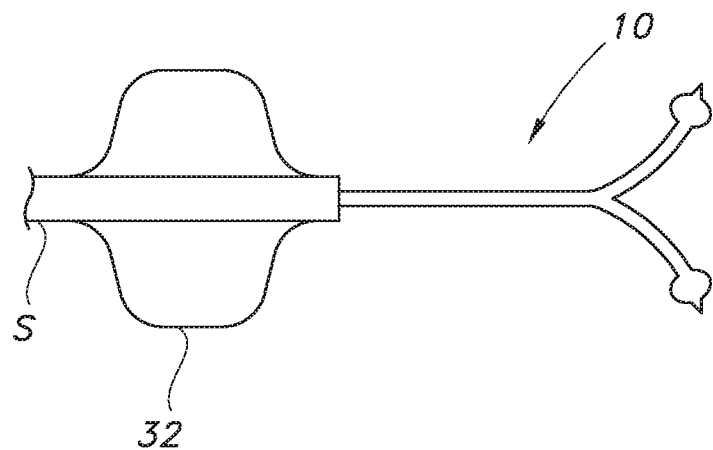
Figure 10:
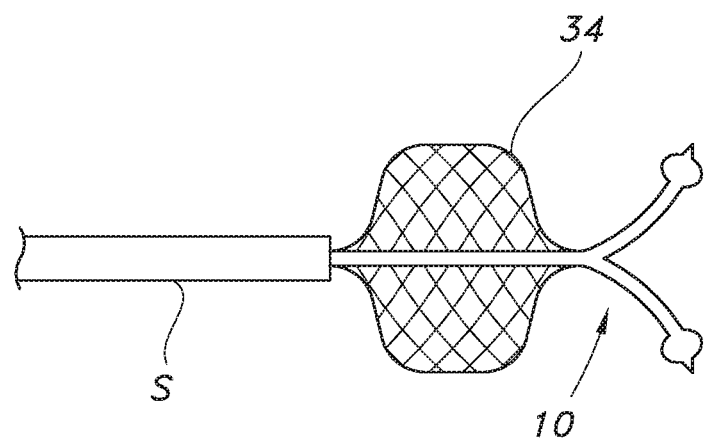
Figure 11:
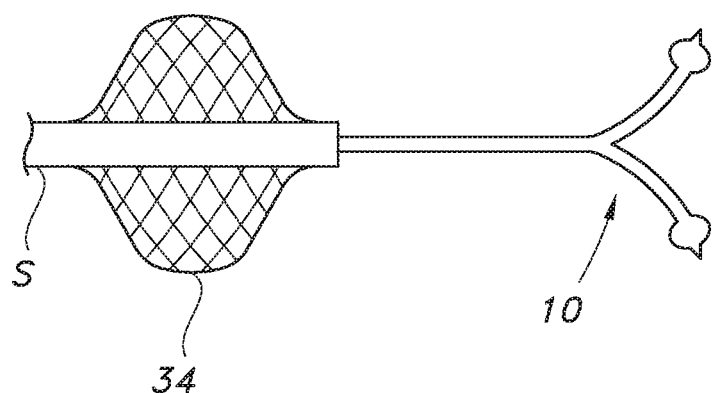

As indicated in FIG. 9, the expandable balloon 32 may also be provided on the sheath S, which may also include an inflation lumen (not shown). FIGS. 10 and 11 further illustrate that, instead of an inflatable balloon 32, the anchor may comprise a self-expanding cage 34. This cage 34 may be provided either on the cutter 10 (FIG. 10) or on the sheath S (FIG. 11).

Figure 12:
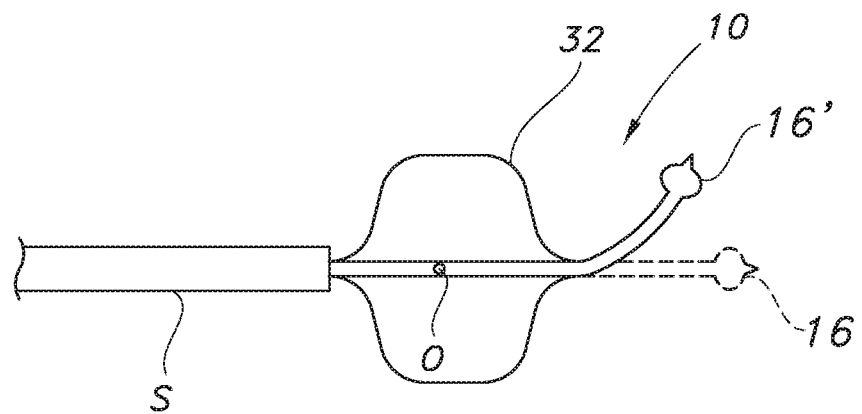

FIGS. 12, 13, 14, and 15 illustrate alternate embodiments. In FIG. 12, the cutter 10 includes only a single expandable arm 16, which may include a blade and limiter as noted above, as well an anchor which may hold the arm in position for scoring or slicing when expanded, such as an expandable (inflatable) balloon 32. Again, radial expansion of the arm 16 (note position 16') may be achieved by using a material that changes shape based on a change in ambient conditions, such as a shape memory material (e.g. Nitinol) that assumes a particular configuration based on a change in temperature (which may be achieved by supplying fluid via sheath S or based on body temperature). In particular, the use of super-elastic Nitinol is possible, which would not require injection of fluid.

Figure 13:
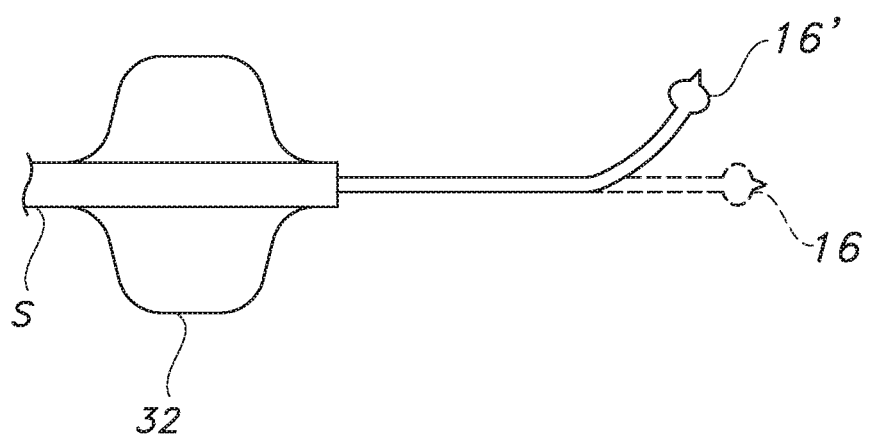
Figure 14:
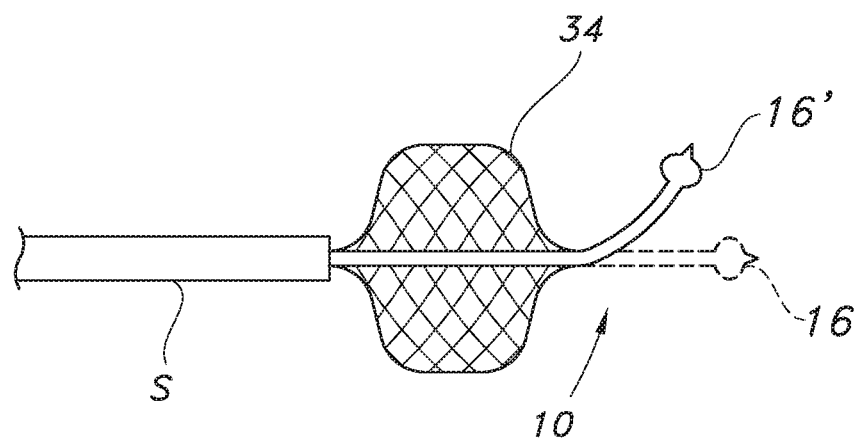
Figure 15:
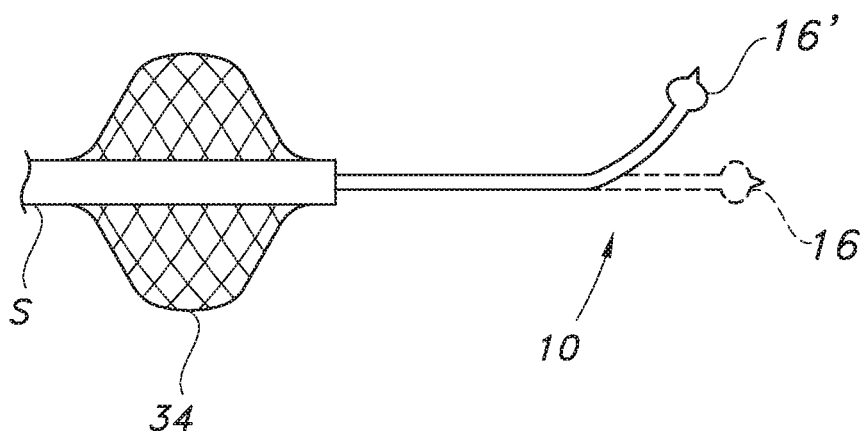

As above, the expandable element may be attached to the shaft 12, and inflation fluid for the balloon 32 may be provided via a lumen in the shaft 12 to an outlet O within the interior compartment of the balloon 32. The balloon 32 may thus be moved through the sheath S in a collapsed or folded configuration, and then expanded within the vessel to provide a positioning function for the associated cutter 10 once expanded. Alternatively, as shown in FIG. 13, the balloon 32 could be attached to the catheter or sheath S, and an expandable cage 34 could alternatively be used, as shown in FIGS. 14 and 15.

In summary, a cutter 10 for cutting a vessel wall and, in particular, for scoring or slicing a lesion in a vessel, is provided. A single shaft 12 includes at least two arms 16, 18, at least one of which includes a blade 20 for scoring or slicing the lesion. Both arms 16, 18 may be provided with blades 20, and limiters may be provided to limit the cutting depth achieved and ensure reliable and repeatable results. More than two arms 16, 18 may also be provided, as may an anchor for aiding in centering the cutter 10 within a vessel undergoing treatment.

The disclosure may be considered to relate to the following items:

1. An apparatus for slicing or scoring a lesion in a vessel, comprising:
   a sheath; and
   a cutter configured to project from the sheath in a deployed position for slicing or scoring the lesion, the cutter including a single shaft connected to a plurality of expandable arms, including a first expandable arm having at least one blade for scoring or slicing the lesion when the cutter is in the deployed position.

2. The apparatus of item 1, wherein the plurality of expandable arms comprise at least two expandable arms forming a Y-shape at a distal end of the single shaft.

3. The apparatus of item 1 or item 2, wherein the first expandable arm includes a pair of blades.

4. The apparatus of any of items 1-3, wherein a second expandable arm includes at least one blade.

5. The apparatus of any of items 1-3, wherein a second expandable arm does not include any blade.

6. The apparatus of any of items 1-5, wherein the first expandable arm includes a limiter configured to limit a cutting depth of the cutter in the deployed position.

7. The apparatus of any of items 1-6, wherein the plurality of expandable arms comprise at least two expandable arms connected to the single shaft at a common bifurcation point.

8. The apparatus of any of the preceding items, wherein the cutter comprises three expandable arms connected to the single shaft.

9. The apparatus of any of the preceding items, wherein the cutter comprises four expandable arms connected to the single shaft.

10. The apparatus of any of the preceding items, wherein the cutter comprises five expandable arms connected to the single shaft.

11. The apparatus of any of items 1-10, further including an anchor configured to anchor the cutter in the vessel.

12. The apparatus of item 11, wherein the anchor comprises an expandable element.

13. The apparatus of item 12, wherein the expandable element comprises an inflatable balloon or an expandable cage.

14. The apparatus of any of items 11 to 13, wherein the anchor is connected to the cutter.

15. The apparatus of any of items 11 to 14, wherein the anchor is connected to the sheath.

16. An apparatus for slicing or scoring a lesion in a vessel, comprising:
   a cutter including a single shaft having a branched portion including at least two expandable arms, a first of the expandable arms including at least one blade for slicing or scoring the lesion when expanded.

17. The apparatus of item 16, further including a sheath configured to receive the cutter.

18. The apparatus of item 16 or item 17, wherein the at least two expandable arms form a Y-shape at a distal end of the single shaft.

19. The apparatus of item 16 or item 17, wherein the first expandable arm includes a pair of blades.

20. The apparatus of any of items 16-19, wherein a second expandable arm includes at least one blade.

21. The apparatus of any of items 16-19, wherein a second expandable arm does not include any blade.

22. The apparatus of any of items 16-19, wherein the first expandable arm includes a limiter configured to limit a cutting depth of the cutter.

23. The apparatus of any of items 16-22, wherein the at least two expandable arms connect to the single shaft at a common bifurcation point.

24. The apparatus of any of items 16-23, wherein the cutter comprises three expandable arms connected to the single shaft.

25. The apparatus of any of items 16-23, wherein the cutter comprises four expandable arms connected to the single shaft.

26. The apparatus of any of items 16-23, wherein the cutter comprises five expandable arms connected to the single shaft.

27. The apparatus of any of items 16-26, further including an anchor configured to anchor the cutter in the vessel.

28. The apparatus of item 27, wherein the anchor comprises an expandable element.

29. The apparatus of item 28, wherein the expandable element comprises an inflatable balloon or an expandable cage.

30. The apparatus of any of items 27 to 29, wherein the anchor is connected to the cutter.

31. The apparatus of any of items 27 to 30, wherein the anchor is connected to a sheath.

32. The apparatus of any of the foregoing items, wherein the cutter comprises a shape memory material.

33. An apparatus for slicing or scoring a lesion in a vessel, comprising:
   a catheter;
   a cutter configured to project from the catheter, the cutter including a first expandable arm including a first blade for slicing or scoring the lesion when expanded.
   an anchor configured to anchor the cutter in the vessel.

34. The apparatus of item 33, wherein the anchor comprises an expandable element.

35. The apparatus of item 33 or item 34, wherein the expandable element comprises an inflatable balloon or an expandable cage.

36. The apparatus of any of items 33-35, wherein the anchor is connected to the cutter.

37. The apparatus of any of items 33-36, wherein the anchor is connected to the catheter.

38. The apparatus of any of items 33-37, wherein the cutter comprises a second expandable arm including a second blade.

39. The apparatus of item 38, wherein the first and second expandable arms form a Y-shape at a distal end of the single shaft.

40. The apparatus of any of items 33-39, wherein the first expandable arm includes a pair of blades.

41. The apparatus of any of items 33-40, wherein the cutter includes a second expandable arm having at least one blade.

42. The apparatus of item any of items 33-41, wherein the cutter includes a second expandable arm that does not include any blade.

43. The apparatus of any of items 33-42, wherein the first expandable arm includes a limiter configured to limit a cutting depth of the cutter.

44. The apparatus of any of items 33-43 or, wherein the cutter comprises a shape memory material.

45. The apparatus of any of items 33-44, wherein the catheter comprises a sheath configured to receive the cutter.

Each of the following terms written in singular grammatical form: "a", "an", and "the", as used herein, means "at least one", or "one or more". Use of the phrase One or more" herein does not alter this intended meaning of "a", "an", or "the". Accordingly, the terms "a", "an", and "the", as used herein, may also refer to, and encompass, a plurality of the stated entity or object, unless otherwise specifically defined or stated herein, or the context clearly dictates otherwise. For example, the phrases: "a unit", "a device", "an assembly", "a mechanism", "a component, "an element", and "a step or procedure", as used herein, may also refer to, and encompass, a plurality of units, a plurality of devices, a plurality of assemblies, a plurality of mechanisms, a plurality of components, a plurality of elements, and, a plurality of steps or procedures, respectively.

Each of the following terms: "includes", "including", "has", "having", "comprises", and "comprising", and, their linguistic/grammatical variants, derivatives, or/and conjugates, as used herein, means "including, but not limited to", and is to be taken as specifying the stated components), feature(s), characteristic(s), parameter(s), integer(s), or step(s), and does not preclude addition of one or more additional component(s), feature(s), characteristic(s), parameter(s), integer(s), step(s), or groups thereof. Each of these terms is considered equivalent in meaning to the phrase "consisting essentially of." Each of the phrases "consisting of" and "consists of, as used herein, means "including and limited to". The phrase "consisting essentially of means that the stated entity or item (system, system unit, system sub-unit device, assembly, sub-assembly, mechanism, structure, component element or, peripheral equipment utility, accessory, or material, method or process, step or procedure, sub-step or subprocedure), which is an entirety or part of an exemplary embodiment of the disclosed invention, or/and which is used for implementing an exemplary embodiment of the disclosed invention, may include at least one additional feature or characteristic" being a system unit system sub-unit device, assembly, sub-assembly, mechanism, structure, component or element or, peripheral equipment utility, accessory, or material, step or procedure, sub-step or sub-procedure), but only if each such additional feature or characteristic" does not materially alter the basic novel and inventive characteristics or special technical features, of the claimed item.

The term "method", as used herein, refers to steps, procedures, manners, means, or/and techniques, for accomplishing a given task including, but not limited to, those steps, procedures, manners, means, or/and techniques, either known to, or readily developed from known steps, procedures, manners, means, or/and techniques, by practitioners in the relevant field(s) of the disclosed invention.

Terms of approximation, such as the terms about, substantially, approximately, etc., as used herein, refers to ±10% of the stated numerical value.

It is to be fully understood that certain aspects, characteristics, and features, of the invention, which are, for clarity, illustratively described and presented in the context or format of a plurality of separate embodiments, may also be illustratively described and presented in any suitable combination or sub-combination in the context or format of a single embodiment. Conversely, various aspects, characteristics, and features, of the invention which are illustratively described and presented in combination or sub-combination in the context or format of a single embodiment may also be illustratively described and presented in the context or format of a plurality of separate embodiments.

Although the invention has been illustratively described and presented by way of specific exemplary embodiments, and examples thereof, it is evident that many alternatives, modifications, or/and variations, thereof, will be apparent to those skilled in the art. Accordingly, it is intended that all such alternatives, modifications, or/and variations, fall within the spirit of, and are encompassed by, the broad scope of the appended claims.

The invention claimed is:

1. An apparatus for slicing or scoring a lesion in a vessel, comprising:
   a sheath; and
   a cutter for projecting from the sheath in a deployed position for slicing or scoring the lesion, the cutter including a single shaft connected to a plurality of expandable arms emanating from the single shaft at a common bifurcation point, the plurality of expandable arms including a first expandable arm having at least one blade for scoring or slicing the lesion when the cutter is in the deployed position;
   wherein a second expandable arm does not include any blade.

2. The apparatus of claim 1, wherein the plurality of expandable arms comprise at least two expandable arms forming a Y-shape at a distal end of the single shaft.

3. The apparatus of claim 1, wherein the first expandable arm includes a pair of blades.

4. The apparatus of claim 1, wherein a second expandable arm includes at least one blade.

5. The apparatus of claim 1, wherein the first expandable arm includes a limiter for limiting a cutting depth of the cutter in the deployed position.

6. The apparatus of claim 1, wherein the cutter comprises three expandable arms connected to the single shaft.

7. The apparatus of claim 1, wherein the cutter comprises four expandable arms connected to the single shaft.

8. The apparatus of claim 1, wherein the cutter comprises five expandable arms connected to the single shaft.

9. The apparatus of claim 1, further including an anchor for anchoring the cutter in the vessel.

10. The apparatus of claim 9, wherein the anchor comprises an expandable element.

11. The apparatus of claim 10, wherein the expandable element comprises an inflatable balloon or an expandable cage.

12. The apparatus of claim 9, wherein the anchor is connected to the cutter.

13. The apparatus of claim 9, wherein the anchor is connected to the sheath.

14. An apparatus for slicing or scoring a lesion in a vessel, comprising:
   a cutter including a single shaft having a branched portion including at least two expandable arms emanating from the single shaft at a common bifurcation point, a first arm of the at least two expandable arms including at least one blade for slicing or scoring the lesion when expanded;
   wherein a second expandable arm does not include any blade.

15. The apparatus of claim 14, further including a sheath for receiving the cutter.

16. The apparatus of claim 14, wherein the at least two expandable arms form a Y-shape at a distal end of the single shaft.

17. The apparatus of claim 14, wherein the first expandable arm includes a pair of blades.

18. An apparatus for slicing or scoring a lesion in a vessel, comprising:
   a catheter;
   a cutter for projecting from the catheter, the cutter including a first expandable arm including a first blade for slicing or scoring the lesion when expanded and a second expandable arm that does not include any blade, wherein the first expandable arm and the second expandable arm emanate from a common bifurcation point; and
   an anchor for anchoring the cutter in the vessel.

* * * * *